US00PP20249P3

(12) United States Plant Patent
Layt

(10) Patent No.: US PP20,249 P3
(45) Date of Patent: Sep. 1, 2009

(54) *PHORMIUM TENAX* PLANT NAMED 'PHOS2'

(50) Latin Name: *Phormium tenax*
Varietal Denomination: PHOS2

(76) Inventor: Todd Anthony Layt, P.O. Box 1011, Richmond NSW 2753 (AU)

( * ) Notice: Subject to any disclaimer, the term of this patent is extended or adjusted under 35 U.S.C. 154(b) by 197 days.

(21) Appl. No.: 11/501,421

(22) Filed: Aug. 9, 2006

(65) Prior Publication Data

US 2007/0050873 P1 Mar. 1, 2007

Related U.S. Application Data

(60) Provisional application No. 60/711,247, filed on Aug. 25, 2005.

(51) Int. Cl.
*A01H 5/00* (2006.01)

(52) U.S. Cl. ..... Plt./373

(58) Field of Classification Search ..... Plt./373
See application file for complete search history.

(56) References Cited

PUBLICATIONS

Layt; "*Phormium tenax* 'PHOS2'" *Plant Varieties Journal* 17 (3): 23, 70 (Oct. 27, 2004).

*Primary Examiner*—Kent L Bell

(57) ABSTRACT

'PHOS2' is a distinctive variety of *Phormium tenax* which is characterized by a dwarf growth habit with a strong shoot density as compared with the species *Phormium tenax,* which has a variable growth form ranging from short to tall plant height and sparse to dense shoot density. In addition, 'PHOS2' has a bronze mature leaf color, whereas the parental form of the species *Phormium tenax* has a mature leaf colour of purple.

1 Drawing Sheet

Latin name of the genus and species: The Latin name of the novel variety disclosed herein is *Phormium tenax.*

Variety denomination: The inventive variety of *Phormium tenax* disclosed herein has been given the varietal denomination 'PHOS2'.

BACKGROUND OF THE INVENTION

The present invention relates to a new and distinct perennial variety of *Phormium tenax,* which has been given the varietal denomination of 'PHOS2'. Its market class is that of an ornamental plant. 'PHOS2' is intended for use in landscaping and as a decorative plant.

Parentage. The *Phormium tenax* variety 'PHOS2' was selected in 2002 in an Australian nursery in the state of New South Wales. 'PHOS2' is a naturally occurring whole mutation selection from open pollinated seedlings of *Phormium tenax.* 'PHOS2' was selected due to its difference in growth habit and colour compared to the parent plant.

Asexual reproduction. 'PHOS2' was first propagated asexually by division in the state of New South Wales, Australia and has since been asexually propagated by division and micropropagation. Divisions of 'PHOS2' root within 3 to 4 weeks.

After divisions were made for several subsequent generations, 'PHOS2' was observed to retain the color and size characteristics that were noted in the original 'PHOS2' seedling. Thus, the distinctive characteristics of the inventive 'PHOS2' variety have remained stable and true to type from generation to generation through successive cycles of asexual reproduction.

An application for plant breeders' rights for variety 'PHOS2' has been filed with the Australian Plant Breeders'

Rights Office, and was first gazetted in the Plant Varieties Journal in August 2004 under Application No. 2004/251.

SUMMARY OF THE INVENTION

'PHOS2' is a distinctive variety of *Phormium tenax* which is characterized by a dwarf growth habit with a strong shoot density as compared with the species *Phormium tenax,* which has a variable growth form ranging from short to tall plant height and sparse to dense shoot density. In addition, 'PHOS2' has a bronze mature leaf color, whereas the parental form of the species *Phormium tenax* has a mature leaf color of purple.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Phormium tenax.*

BOTANICAL DESCRIPTION OF THE PLANT

Figure 1:
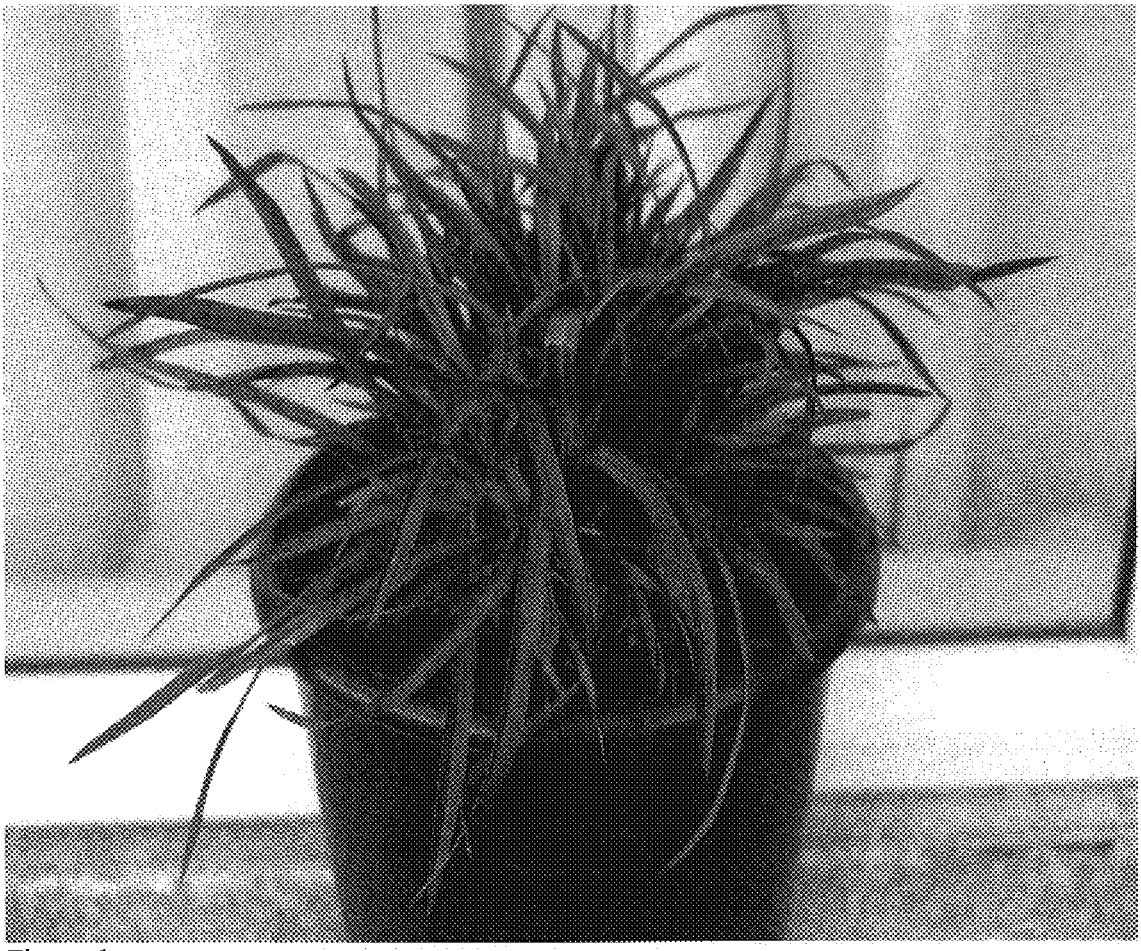
FIG. 1 shows an exemplary'PHOS2' plant.

The following is a detailed botanical description of a new and distinct variety of a *Phormium tenax* ornamental plant known as 'PHOS2'. Plant observations were made on plants grown in New South Wales, Australia. Unless indicated otherwise, the descriptions disclosed herein are based upon observations made of mature 'PHOS2' plants, 26 weeks old, grown in nursery pots and field plots.

Those skilled in the art will appreciate that certain characteristics will vary with older or, conversely, younger plants.

'PHOS2' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like. Color notations are based on The Royal Horticultural Society Colour Chart, (The Royal Horticultural Society, London, 1995 edition).

'PHOS2' is a perennial *Phormium tenax* plant, which is a seedling selection from the species *Phormium tenax* purple form. After its selection, 'PHOS2' was asexually propagated by division and then by micropropagation. 'PHOS2' has a dwarf growth habit, strong shoot density and an immature green leaf colour that matures to bronze. A botanical description of 'PHOS2' and a comparison with other varieties of *Phormium tenax* are provided below. A representative 'PHOS2' plant is shown in FIG. 1.

Botanical Description of the Variety

Growth habit: 'PHOS2' is a dwarf, rhizomatous plant forming an upright dense tuft. Average plant height is 18–25 cm and average plant spread is 20–25 cm in a mature plant grown in a 150 mm nursery or field pot in Sydney, New South Wales, Australia.

Leaves: The upper side of the mature leaf is brown in colour (RHS 200C) and the under side leaf color is RHS N199B. When immature, the upper side of the leaf is green in colour (RHS 144A) and the under side leaf color is RHS 144B. The leaf is generally 6–8 mm in width, and reaches an average length of 18–20 cm. The leaf shape is linear-ensiform, the leaf base is cauline and therefore lacks the presence of a petiole, the leaf margin is entire, the leaf apex is acute and the leaf surface texture is characterised by fine striations. The leaf venation pattern is parallel and the venation color is the same as the rest of the leaf. The leaf attitude is erect to semi-erect. The color of the base of the shoot where the leaves unite is yellow-green (RHS144C).

Roots: The roots of 'PHOS2' are fleshy and thick, similar to other *Phormium tenax*.

Flowers: No flowers have been produced.

Environmental tolerances: 'PHOS2' has typical shade tolerance for the species. 'PHOS2' has been observed to hold color to −8 degrees Celsius without any noticeable change in appearance of the plant. 'PHOS2' has moderate to good drought tolerance. 'PHOS2' has moderate to good recovery with watering after severe wilting. 'PHOS2' does well in sandy soils, but also tolerates heavy, clay-type soils well.

Pest resistance: 'PHOS2' has average resistance to pests similar to *Phormium tenax*.

These features and other characteristics of the plant are apparent from the figure.

Comparison of 'PHOS2' with Other Varieties of *Phormium tenax*

'PHOS2' has a more dwarf growth habit, stronger shoot density and a green immature leaf color changing to a bronze mature leaf color, whereas the species *Phormium tenax* is taller, less dense and usually purple in leaf colour (colors ranging from greyed-purple to brown).

'PHOS2' has a more dwarf growth habit and greater shoot density than another comparable type of *Phormium tenax,* known as 'Chocolate Fingers' (unpatented). 'PHOS2' has a plant height of 18–25 cm and plant width of 20–25 cm, whereas 'Chocolate Fingers' has a plant height of 30 cm and plant width of 30 cm. 'PHOS2' has an upper side mature leaf color of brown (RHS 200C), whereas the upper side mature leaf colour of 'Chocolate Fingers' is a slightly lighter brown (approximately RHS 200D).

The combination of its dwarf growth habit, strong shoot density and bronze mature leaf color makes 'PHOS2' a desirable ornamental plant suited for mass production for pot and landscape use.

That which is claimed is:

1. A new and distinct variety of *Phormium tenax* plant named 'PHOS2', substantially as described and illustrated herein.

* * * * *